US012599743B2

(12) United States Patent
Lee et al.

(10) Patent No.: US 12,599,743 B2
(45) Date of Patent: Apr. 14, 2026

(54) BIDIRECTIONAL FLOW-CONTROLLABLE ARTIFICIAL RESPIRATOR

(71) Applicant: Korea University Research and Business Foundation, Seoul (KR)

(72) Inventors: Jang Woo Lee, Seoul (KR); Yoon Je Lee, Seoul (KR)

(73) Assignee: Korea University Research and Business Foundation (KR)

( * ) Notice: Subject to any disclaimer, the term of this patent is extended or adjusted under 35 U.S.C. 154(b) by 1095 days.

(21) Appl. No.: 17/635,877

(22) PCT Filed: Aug. 14, 2020

(86) PCT No.: PCT/KR2020/095107
§ 371 (c)(1),
(2) Date: Feb. 16, 2022

(87) PCT Pub. No.: WO2021/034172
PCT Pub. Date: Feb. 25, 2021

(65) Prior Publication Data
US 2022/0288347 A1      Sep. 15, 2022

(30) Foreign Application Priority Data

Aug. 16, 2019      (KR) ........................ 10-2019-0100334
Aug. 11, 2020      (KR) ........................ 10-2020-0100359

(51) Int. Cl.
*A61M 16/20*            (2006.01)
*A61M 16/00*            (2006.01)
*A62B 18/10*            (2006.01)

(52) U.S. Cl.
CPC ........ *A61M 16/20* (2013.01); *A61M 16/0069* (2014.02); *A62B 18/10* (2013.01)

(58) Field of Classification Search
CPC ..... A61H 31/007; G09B 23/288; A62B 18/10
See application file for complete search history.

(56) References Cited

U.S. PATENT DOCUMENTS 6,230,708 B1 *    5/2001    Radko ................. A61M 16/206
                                                                    128/205.24
6,604,523 B2 *    8/2003    Lurie ..................... C09K 5/042
                                                                    128/205.24
(Continued)

FOREIGN PATENT DOCUMENTS

CN            204815227 U      12/2015
JP            H0747126 A   *    2/1995   ............ A61M 16/20
(Continued)

OTHER PUBLICATIONS

Extended European Search Report issued Jul. 24, 2023; in EP application No. 20854741.4 filed Aug. 14, 2020, 10 pages.
(Continued)

*Primary Examiner* — Brandy S Lee
*Assistant Examiner* — Mishal Zahra Hussain
(74) *Attorney, Agent, or Firm* — Thorpe North & Western, LLP

(57)            ABSTRACT

A bidirectional flow-controllable artificial respirator, according to one embodiment, comprises: a chamber for storing air; a tube connected to the chamber and having air flowing therein; a mask connected to the tube and mounted on a face or mouth; and a flow control valve unit provided in the tube and controlling the air flow between the chamber or an air supply source, and the mask. The flow control valve unit comprises: a first valve allowing an air supply path from the air supply source toward the mask; and a second valve allowing an air discharge path from the mask toward the outside of the respirator, wherein the first valve and the second valve are alternately opened and closed during artificial respiration, the first valve is blocked during chest compressions so that negative pressure in a subject receiving air is maintained for a long period, and the first valve and the second valve may be selectively opened and closed so as to (Continued)

allow air to be supplied according to a preset air supplying period.

6 Claims, 5 Drawing Sheets

(56)                    References Cited

U.S. PATENT DOCUMENTS

| 8,875,708 | B2 * | 11/2014 | Nysaether | A61M 16/201 |
| | | | | 128/205.24 |
| 9,308,345 | B2 | 4/2016 | Chalvignac | |
| 2002/0069878 | A1 | 6/2002 | Lurie et al. | |
| 2007/0056588 | A1 * | 3/2007 | Hayek | A61M 16/06 |
| | | | | 128/205.25 |

| 2009/0266364 | A1 | 10/2009 | Nysaether et al. | |
| 2011/0259339 | A1 | 10/2011 | Isaza | |
| 2014/0069428 | A1 * | 3/2014 | Sears | F16K 11/0873 |
| | | | | 128/204.21 |

FOREIGN PATENT DOCUMENTS

| JP | 2000-152993 | A | 6/2000 |
| JP | 2012-530556 | A | 12/2012 |
| JP | 2012-531250 | A | 12/2012 |
| KR | 10-2012-0015794 | A | 8/2013 |
| KR | 10-2018-0041535 | A | 4/2018 |
| WO | WO 2008/130937 | A2 | 10/2008 |

OTHER PUBLICATIONS

International Search Report for International Application No. PCT/KR2020/095107 dated Nov. 26, 2020, 12 pages.

* cited by examiner

1

BIDIRECTIONAL FLOW-CONTROLLABLE ARTIFICIAL RESPIRATOR

TECHNICAL FIELD

Disclosed is a bidirectional flow-controllable artificial respirator.

BACKGROUND ART

Cardiopulmonary resuscitation (CPR) is performed to a patient, who cannot spontaneously breathe, to supply oxygen to the patient and maintain the patient's blood flow. In this case, together with chest compression, an air mask bag unit (AMBU) is generally used to induce breathing.

The AMBU refers to a manual artificial respiration device to supply air by applying positive pressure to the lungs by using an airbag in a state in which a mask covers the nose and the mouth. The chest compression is temporarily stopped at the time of supplying air. The chest compression is performed again after sufficiently supplying air into the lungs. This process is repeated to induce the patient's breathing.

An important thing in the above-mentioned cardiopulmonary resuscitation including the artificial respiration method is to maintain a minimum blood flow toward a cerebral blood vessel while chest compression and relaxation are repeated, to maintain a blood flow toward the coronary artery during chest relaxation, and to appropriately supply oxygen.

As a related technology, Korean Patent Application Publication No. 10-2018-0041535 filed on Oct. 14, 2018, discloses "Flow Control Manual Artificial Respiration Device Via Feedback and Method of Injecting Artificial Respiration Using the Same".

The above-mentioned background art is technical information that the inventors have retained to derive the present invention or have obtained in the course of deriving the present invention, and cannot be thus said to be technical information publicly known to the public before filing the invention.

DISCLOSURE OF THE INVENTION

Technical Goals

An object of the embodiment is to provide an artificial respirator capable of selectively cutting off a supply of air into the lungs while chest compression is performed during artificial respiration.

Another object of the embodiment is to provide an artificial respirator capable of selectively allowing a supply of air into the lungs while chest relaxation is performed during artificial respiration.

Still another object of the embodiment is to provide an artificial respirator capable of allowing an appropriate amount of air to be naturally supplied by negative pressure in the lungs during artificial respiration.

Yet another object of the embodiment is to provide an artificial respirator capable of consistently supplying air while chest compression and relaxation are repeated.

Still yet another object of the embodiment is to provide an artificial respirator capable of maintaining negative pressure in the lungs for a long period after ventilation.

A further object of the embodiment is to provide an artificial respirator capable of maintaining an appropriate blood flow rate to the cerebral blood vessel and the coronary artery.

Technical problems to be solved by the embodiments are not limited to the is aforementioned technical problem, and other technical problems, which are not mentioned above, may be clearly understood by those skilled in the art from the following descriptions.

Technical Solutions

According to an aspect, there is provided a bidirectional flow-controllable artificial respirator including: a chamber to store air; a tube connected to the chamber such that the air flows therein; a mask connected to the tube to be mounted around a face or oral cavity; and a flow control valve unit disposed in the tube to control a flow of air between the mask and the chamber or an air supply source, in which the flow control valve unit includes: a first valve to allow an air supply path from the air supply source toward the mask; and a second valve to allow an air discharge path from the mask to the outside of the artificial respirator, in which the first and second valves are alternately opened or closed during artificial respiration, in which the first valve is closed during chest compression so that negative pressure in a subject receiving air is maintained for a long period, and in which the first and second valves are selectively opened or closed to allow a supply of air according to a preset air supply period.

According to the embodiment, the bidirectional flow-controllable artificial respirator may further include a measurement sensor disposed in the tube to measure a flow velocity of the air passing through the flow control valve unit or a pressure applied to a respiratory tract.

According to the embodiment, the first valve may include: a first transmission part through which the air passes when the air is supplied from the air supply source toward the mask; a first opening/closing part disposed in the first transmission part to allow a flow only in one direction from the air supply source to the mask; and a first control part disposed in the first transmission part and spaced apart from the first opening/closing part, and when the supply of air is cut off during chest compression and when the pressure measured by the measurement sensor reaches a preset pressure during chest relaxation, the first control part may selectively control the supply of air through the first opening/closing part so that the supply of air is allowed according to the preset air supply period.

According to the embodiment, the second valve may include: a second transmission part through which the air passes when the air is discharged to the outside from the mask; a second opening/closing part disposed in the second transmission part to allow a flow only in one direction from the mask to the outside; and a second control part disposed in the second transmission part and spaced apart from the second opening/closing part, and the second control part may selectively control a discharge of air through the second opening/closing part so that the discharge of air is allowed during chest compression and the discharge of air is cut off according to the preset air supply period.

According to the embodiment, the first control part may be closed during chest compression to cut off the supply of air through the first opening/closing part, the first control part may be opened at a preset point in time of the supply of air to allow the supply of air through the first opening/closing part, the first control part may be closed to maintain negative pressure in the subject receiving air for a long period when a point in time is not the point in time of the supply of air, the second control part may be opened during chest compression to allow the discharge of air through the second opening/closing part, the second control part may be closed at the preset point in time of the supply of air to cut off the discharge of air through the second opening/closing part, and the second control part may be opened to improve efficiency in supplying air when a point in time is not the point in time of the supply of air.

According to the embodiment, the first control part or the second control part may include a single rotary plate to block an air transmission path.

According to the embodiment, the first control part may include a first rotary plate to open or close the first transmission part, the second control part may include a second rotary plate to open or close the second transmission part, and the first and second rotary plates may be disposed to be orthogonal to each other and rotate together by means of a rotary shaft to connect the first and second rotary plates.

According to the embodiment, the first control part or the second control part may include a locking element to fix a closed state of the first opening/closing part or the second opening/closing part.

According to the embodiment, the locking element may fix the closed state of the first opening/closing part or the second opening/closing part by rotating.

According to the embodiment, the locking element may fix the closed state of the first opening/closing part or the second opening/closing part by sliding.

Advantageous Effects

According to the bidirectional flow-controllable artificial respirator according to the embodiment, it is possible to selectively cut off a supply of air into the lungs while chest compression is performed during artificial respiration.

According to the bidirectional flow-controllable artificial respirator according to the embodiment, it is possible to selectively allow a supply of air into the lungs while chest relaxation is performed during artificial respiration.

According to the bidirectional flow-controllable artificial respirator according to the embodiment, it is possible to allow an appropriate amount of air to be naturally supplied by negative pressure in the lungs during artificial respiration.

According to the bidirectional flow-controllable artificial respirator according to the embodiment, it is possible to consistently supply air while chest compression and relaxation are repeated.

According to the bidirectional flow-controllable artificial respirator according to the embodiment, it is possible to maintain negative pressure in the lungs for a long period after ventilation.

According to the bidirectional flow-controllable artificial respirator according to the embodiment, it is possible to maintain an appropriate blood flow rate toward the cerebral blood vessel and the coronary artery.

The effects of the bidirectional flow-controllable artificial respirator according to the embodiment are not limited to the aforementioned effects, and other effects, which are not mentioned above, may be clearly understood by those skilled in the art from the following descriptions.

4

Figure 3:
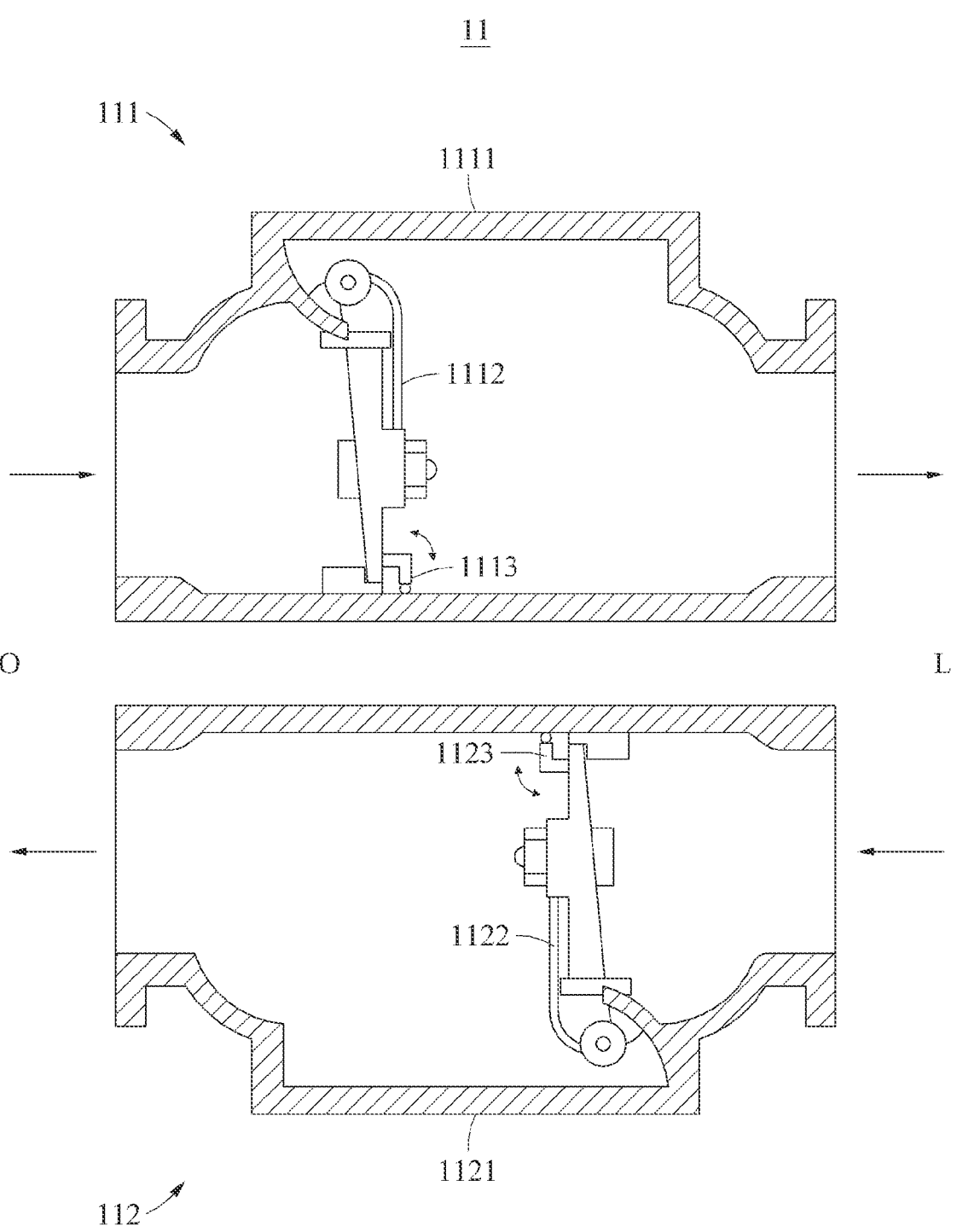

FIG. 3 is a schematic longitudinal sectional view of a flow control valve unit according to Embodiment 2.

Figure 4:
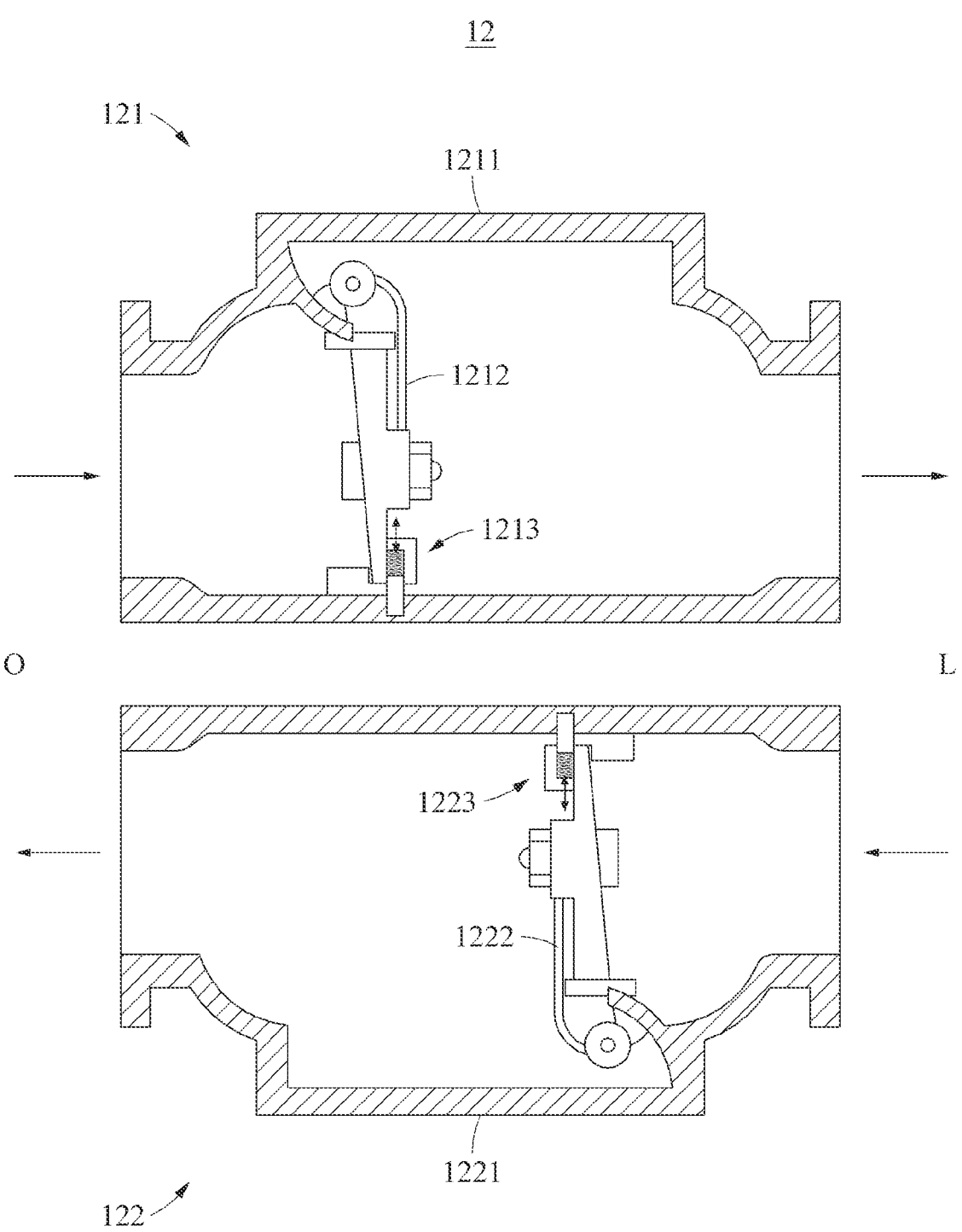

FIG. 4 is a schematic longitudinal sectional view of a flow control valve unit according to Embodiment 3.

FIG. 5 is a schematic transverse cross-sectional view of a flow control valve unit according to Embodiment 4.

The following drawings attached to the present specification illustrate exemplary embodiments of the present invention and serve to further understand the technical spirit of the present invention together with the detailed description of the present invention, and the present invention should not be interpreted as being limited to the items illustrated in the drawings.

BEST MODE FOR CARRYING OUT THE INVENTION

Hereinafter, embodiments will be described in detail with reference to the illustrative drawings. In giving reference numerals to constituent elements of the respective drawings, it should be noted that the same constituent elements will be designated by the same reference numerals, if possible, even though the constituent elements are illustrated in different drawings. Further, in the following description of the embodiments, a detailed description of publicly known configurations or functions incorporated herein will be omitted when it is determined that the detailed description obscures the subject matters of the embodiments.

In addition, the terms first, second, A, B, (a), and (b) may be used to describe constituent elements of the embodiments. These terms are used only for the purpose of discriminating one constituent element from another constituent element, and the nature, the sequences, or the orders of the constituent elements are not limited by the terms. When one constituent element is described as being "connected", "coupled", or "attached" to another constituent element, it should be understood that one constituent element can be connected or attached directly to another constituent element, and an intervening constituent element can also be "connected", "coupled", or "attached" to the constituent elements.

The constituent element, which has the same common function as the constituent element included in any one embodiment, will be described by using the same name in other embodiments. Unless disclosed to the contrary, the configuration disclosed in any one embodiment may be applied to other embodiments, and the specific description of the repeated configuration will be omitted.

A general artificial respirator may include an airbag, a valve, a mask, and the like.

The airbag is automatically filled with air and may supply air to be injected into the lungs.

The valve blocks exhaled air from a patient and allows only air in the airbag to flow.

The mask may be connected to the valve and worn around the patient's mouth.

A user of the artificial respirator may adjust the amount of air to be supplied to the patient by adjusting a degree to which the user presses the airbag and a speed at which the user presses the airbag.

In addition, when high-concentration oxygen is required, an oxygen tank or the like may be coupled to the airbag by connecting a line.

Figure 1:
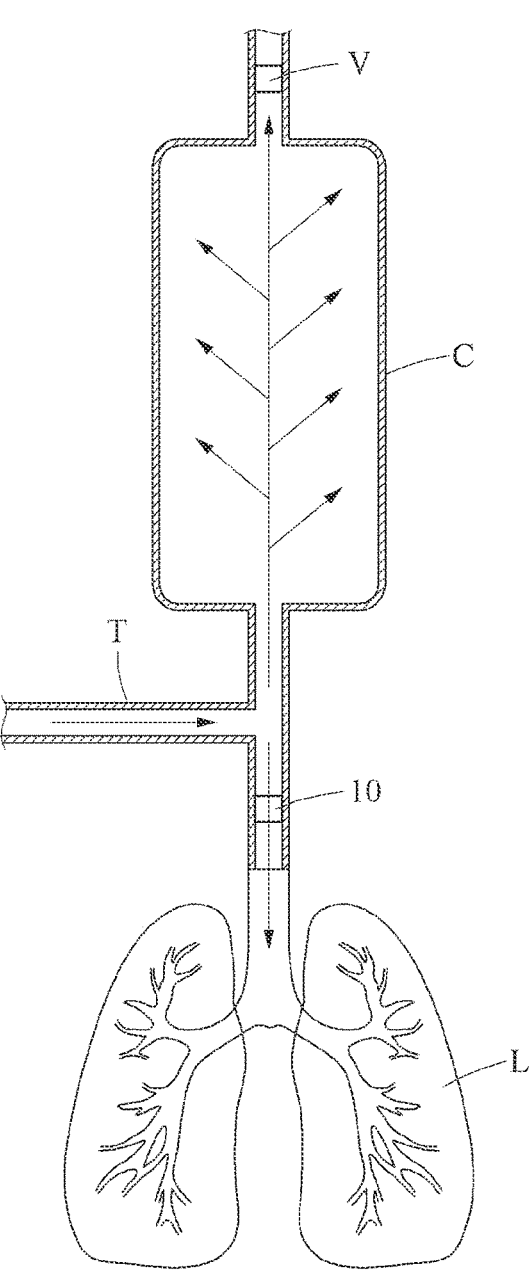
FIG. 1 is a view schematically illustrating an artificial respirator having a flow control valve unit according to one embodiment.

FIG. 1 is a view schematically illustrating an artificial respirator 1 having a flow control valve unit 10 according to the embodiment.

In this case, the artificial respirator 1 according to the embodiment may be used to supply air to a subject receiving air that needs to receive air. The artificial respirator 1 may be connected to an air supply source disposed outside the artificial respirator 1.

For example, the subject receiving air may be a patient's lungs, and the air supply source may be an oxygen tank or outside air.

Referring to FIG. 1, the artificial respirator 1 having the flow control valve unit 10 according to the embodiment may include a chamber C, a tube T, a mask (not illustrated), a flow control valve unit 10, and a chamber valve V.

The chamber C may be a bag that stores air.

In this case, the chamber C may store air introduced from the air supply source, and the stored air may be supplied into the lungs at the time of supplying air.

The tube T may be a tube connected to the air supply source to allow the air supply source to communicate with the lungs L or allow the chamber C to communicate with the patient's lungs L. Therefore, the air may flow into the lungs L from the outside or flow to the outside from the lungs L through the tube T.

One side of the mask (not illustrated) is connected to the tube T and the other side the mask may be mounted around the patient's face or oral cavity. Therefore, the air may flow from the air supply source to the mask through the tube T and then be supplied into the lungs through the patient's respiratory tract. Further, the air may be discharged from the lungs and then discharged to the outside through the mask and the tube T.

The flow control valve unit 10 may be disposed in the tube T and control a flow of air supplied into the patient's lungs L or a flow of air discharged from the patients lungs L.

For example, the flow control valve unit 10 may be a combination of two check valves each to allow a flow only in one direction. For example, each of the check valves constituting the flow control valve unit 10 may be provided as a swing check valve.

The flow control valve unit 10 will be described below in more detail with reference to FIGS. 2 to 4.

The chamber valve V may be installed at one side of the chamber C to control the amount of air in the chamber C. The chamber valve V is maintained in a closed state at normal times. However, when the supply of air is continuously performed and both the lungs L and the chamber C are fully filled with air, the chamber valve V is opened to discharge a part of the air.

In addition, the artificial respirator 1 according to the embodiment may further include a first sensor (not illustrated) and a second sensor (not illustrated).

The first sensor may be provided in the tube T and disposed at a position adjacent to the flow control valve unit 10. The first sensor may measure a flow velocity of the air passing through the flow control valve unit 10. For example, the first sensor may be provided as a flow sensor.

The second sensor may be provided in the tube T and disposed to be closer to the respiratory tract than is the first sensor. The second sensor may measure a pressure applied in the respiratory tract. For example, the second sensor may be provided as a pressure sensor.

The electronic system including the first and second sensors may control the flow of air in the flow control valve unit 10 of the artificial respirator 1.

For example, the electronic system may control the flow control valve unit 10 so that the flow control valve unit 10 induces a flow of intake air by being synchronized with the chest relaxation in a 10-second cycle while the chest compression and relaxation are repeated.

In addition, when the pressure measured by the second sensor reaches a preset pressure, the flow control valve unit 10 may be controlled to induce the flow of intake air at the chest relaxation timing. Then, when the pressure in the respiratory tract becomes higher than a reference pressure by the flow of intake air, the flow control valve unit 10 may be controlled to return the state back to the original state.

In addition, as the flow control valve unit 10, a mechanical valve opening/closing device may be applied, which manually opens or closes the valve at the chest relaxation timing after the chest compression and relaxation are repeated ten times, for example.

Figure 2:
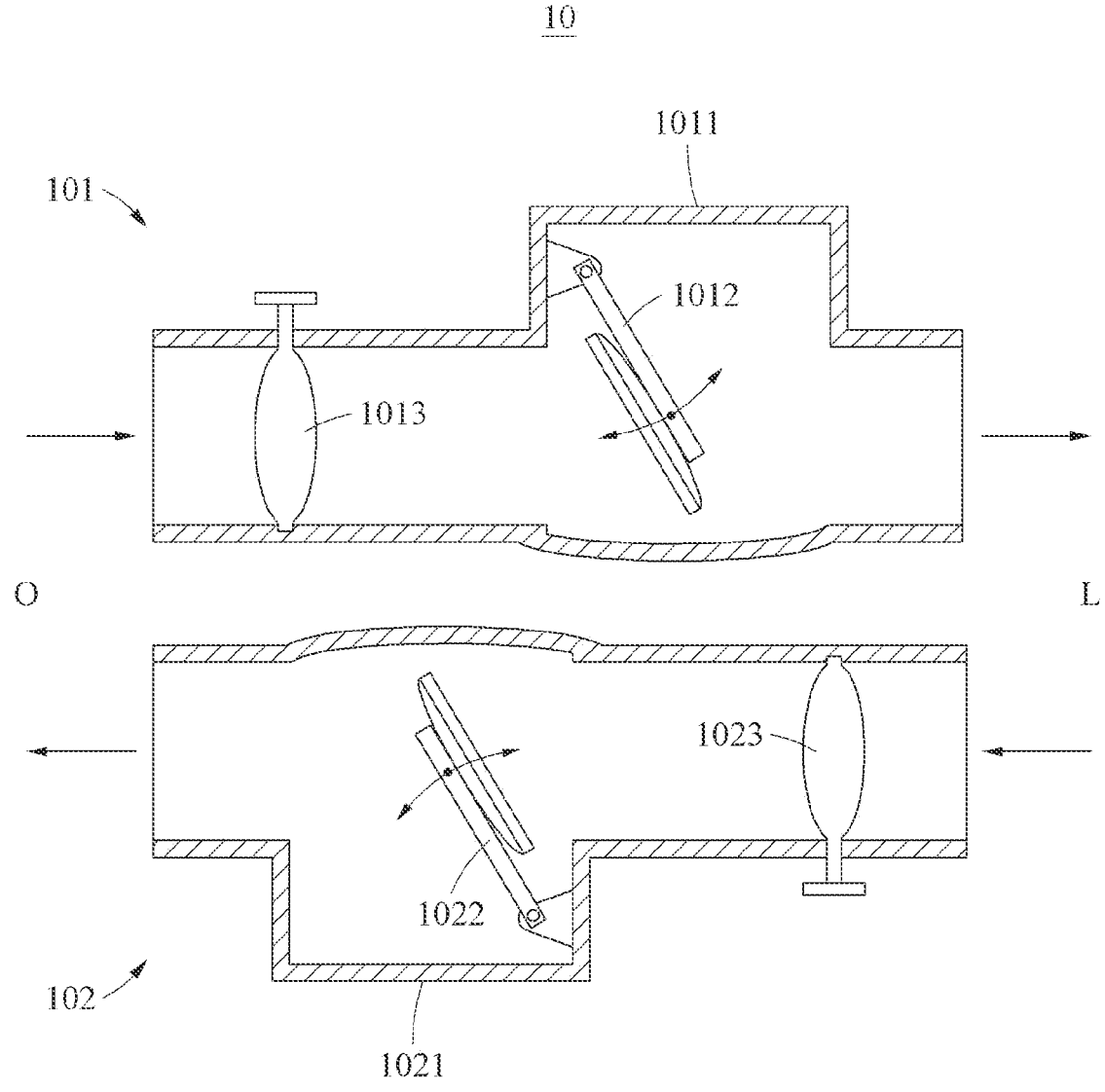
FIG. 2 is a schematic longitudinal sectional view of a flow control valve unit according to Embodiment 1.

FIG. 2 is a schematic longitudinal sectional view of the flow control valve unit 10 according to Embodiment 1.

Referring to FIG. 2, the flow control valve unit 10 according to Embodiment 1 may include a first valve 101 and a second valve 102.

The first and second valves 101 and 102 may each be provided as the same check valve. In addition, the first and second valves 101 and 102 may constitute the flow control valve unit 10 by being coupled to be disposed in opposite directions.

In this case, the first and second valves 101 and 102 may each be provided as a one-way valve that allows a flow from one side to the other side of the valve but does not allow the reverse flow. For example, the first and second valves 101 and 102 may each be a swing check valve.

The first valve 101 may allow an air supply path from an air supply source O to the inside of the lungs L.

Specifically, the first valve 101 may include a first transmission part 1011, a first opening/closing part 1012, and a first control part 1013.

The first transmission part 1011 may define a body of the first valve 101 and have openings formed at two opposite sides thereof. The air may be introduced into the first transmission part 1011 from the air supply source O through one opening and discharged through the other opening. The air may pass through the first transmission part 1011 so as to be supplied into the lungs L.

The first opening/closing part 1012 may be disposed in the first transmission part 1011 and include a disc, a hinge, a seat, and the like.

The disc serves to substantially block or allow a flow path of a fluid.

The hinge may be fixed to the transmission part 1011 and connected to one side of the disc so that the disc may rotate about the hinge, as a rotation center, when the disc allows the flow in one direction or blocks the flow in the other direction.

The seat may be fixed to the transmission part 1011 and support the disc at the other side of the disc so that the disc blocks the flow in the other direction.

The first opening/closing part 1012 configured as described above may rotate so that the air may flow only into the lungs L from the air supply source O. That is, the first opening/closing part 1012 may be autonomously opened when the flow rate of the air is equal to or higher than a predetermined flow rate when the air flows from the air supply source O to the lungs L. On the contrary, when the air flows in the direction in which the air is discharged from the lungs L, the first opening/closing part 1012 may be maintained in the closed state by being caught by a support part disposed in the first transmission part 1011.

The first control part 1013 may be disposed in the first transmission part 1011 and spaced apart from the first opening/closing part 1012. The first control part 1013 may be manually or automatically opened or closed and control the flow of air through the first opening/closing part 1012. That is, the first control part 1013 may be closed to block the air supply path so that the air is not supplied into the lungs L even though the flow from the air supply source O toward the lungs L is generated.

The second valve 102 may allow an air discharge path from the inside of the lungs L to the outside O of the artificial respirator.

Specifically, the second valve 102 may include a second transmission part 1021, a second opening/closing part 1022, and a second control part 1023.

The second transmission part 1021 may define a body of the second valve 102 and have openings formed at two opposite sides thereof. The air may be introduced into the second transmission part 1021 through one opening from the inside of the lungs L. The air may pass through the second transmission part 1021 so as to be discharged through the other opening.

The second opening/closing part 1022 may be disposed in the second transmission part 1021 and include a disc, a hinge, a seat, and the like, like the first opening/closing part 1012.

The second opening/closing part 1022 may rotate so that the air may flow only to the outside O from the inside of the lungs L. That is, the second opening/closing part 1022 may be autonomously opened when the flow rate of the air is equal to or higher than a predetermined flow rate when the air flows from the inside of the lungs L to the outside O. On the contrary, when the air flows in the direction in which the air is supplied from the air supply source O, the opening/closing, part 1022 may be maintained in the closed state by being caught by a support part disposed in the second transmission part 1021.

The second control part 1023 may be disposed in the second transmission part 1021 and spaced apart from the second opening/closing part 1022. The second control part 1023 may be manually or automatically opened or closed and control the flow of air through the second opening/closing part 1022. That is, the second control part 1023 may be closed to block the air discharge path so that the air is not discharged to the outside O even though the flow from the lungs L toward the outside O is generated.

The flow control valve unit 10 including the above-mentioned configuration may operate similar to a 3-state buffer in respect to the flow of air and be controlled by electrical or mechanical methods or the like from the outside.

In the present specification, the supply of air means that the air flows from the air supply source O into the lungs L through the first valve 101, and the discharge of air means that the air flows from the inside of the lungs L to the outside O through the second valve 102. Hereinafter, a detailed description of the flow directions of air will be omitted.

The first and second valves 101 and 102 may be alternately opened or closed during artificial respiration.

For example, during chest compression, the first valve 101 may block the air supply path, and the second valve 102 may allow the discharge path. Therefore, during chest compression, only the discharge path of the air in the lungs is allowed, such that a negative pressure state in the lungs for a long period.

In addition, the first and second valves 101 and 102 may be selectively opened or closed to allow the supply of air according to a preset air supply period.

Specifically, the artificial respirator 1 according to the embodiment may set the air supply period. In this case, the period may be the time or the number of times of chest compression. For example, the air supply period 10 seconds. Therefore, when the supply of air is performed once at the time of performing the chest compression as cardiopulmonary resuscitation and simultaneously using the artificial respirator 1, the air may be supplied again when 10 seconds elapse after a point in time at which the air is supplied. That is, the first valve 101 may be opened at the point in time of the supply of air, maintained in the closed state while the chest compression and relaxation are repeated and then opened again at the point in time of the supply of air after 10 seconds elapse. On the contrary, the second valve 102 may be maintained in the opened state while the chest compression and relaxation are repeated, and then closed at the point in time of the supply of air.

In this case, the air may be naturally supplied at the point in time of chest relaxation without applying positive pressure.

Specifically, the lungs supplied with the air may be in a positive pressure state. Since only the air discharge path is allowed during chest compression as described above, the pressure in the lungs may be decreased to a negative pressure state as the chest compression is repeated. In this state, when the first valve 101 is opened according to the air supply period, the air may be naturally supplied, by a difference in pressure, from the air supply source O connected to the artificial respirator 1.

The first control pad 1013 is a component to control the air supply path through the first valve 101, and the second control part 1023 is a component to control the air discharge path through the second valve 102.

Specifically, the first control part 1013 is closed during chest compression, such that the air supply path may be blocked in advance so that the pressure difference prevents the air from passing through the first opening/closing part 1012 even though the negative pressure is generated in the lungs L. In contrast, the first control part 1013 is opened at a preset point in time of the supply of air, such that the air supply path may be normally allowed so that the air passes through the first opening/closing part 1012. In addition, the first control part 1013 is maintained in the closed state during chest relaxation even though the current point in time is not the point in time of the supply of air, such that the first valve 101 may be closed so that the air is not introduced into the lungs.

In contrast to the first control part 1013, the second control part 1023 is opened during chest compression, such that the air discharge path of the second valve 102 may be allowed so that the air may be discharged consistently from the inside of the lungs L to while passing through the second opening/closing part 1022. In contrast, the second control part 1023 is closed at the preset point in time of the supply of air, such that the air discharge path may be blocked in advance so that the pressure difference from the outside prevents the air from passing through the second opening/closing part 1022 even though the positive pressure is generated in the lungs L.

Therefore, the use of the bidirectional flow-controllable artificial respirator 1 including the flow control valve unit 10 according to the embodiment may maintain the inside of the lungs L in the negative pressure state for a long period and improve the efficiency in supplying air into the lungs while the chest compression and relaxation are repeated. In addition, it is possible to supply air naturally according to the patient's chest relaxation without artificially applying a positive pressure to supply the air.

Referring back to FIG. 2, the first and second control parts 1013 and 1023 of the flow control valve unit 10 according to Embodiment 1 may each include a single rotary plate.

Specifically, the rotary plate may be provided as a single circular plate. A shaft may be provided at a central portion of the first control part 1013 or the second control part 1023 and have a diameter equal to a diameter of the first control part 1013 or the second control part 1023, and the rotary plate may be coupled to the shaft so that the shaft penetrates the rotary plate so as to be parallel to the rotary plate. The rotary plate may rotate about the shaft as a central axis. The rotary plate may rotate to be parallel to the first control part 1013 or the second control part 1023 to close the first control part 1013 or the second control part 1023. The rotary plate may rotate to be perpendicular to the first control part 1013 or the second control part 1023 to open the first control part 1013 or the second control part 1023. Therefore, the air supply path may be blocked or allowed.

As another example, the rotary plate is not the single rotary plate provided on each of the first and second control parts 1013 and 1023, but orthogonal rotary plates connected to a single shaft, provided to be shared by the first and second control parts 1013 and 1023, to alternately open or close the first and second control parts 1013 and 1023.

Specifically, the orthogonal rotary plates may include first and second rotary plates.

Both the first and rotary plates may each be provided as a circular plate. A single straight shaft may be provided at the central portions of the first and second control parts 1013 and 1023 and having a diameter equal to a diameter of each of the first and second control parts 1013 and 1023. The first and rotary plates may be coupled to the shaft so that the shaft penetrates the first and rotary plates so as to be parallel to the first and rotary plates, such that the first and rotary plates may be arranged side by side on the shaft. In this case, the first and rotary plates may be disposed such that the planes thereof are orthogonal to each other.

The first and rotary plates fixed as described above may rotate together about a single rotation axis.

The first control part 1013 may be closed when the first rotary plate rotates to be parallel to the first control part 1013. In this case, since the second rotary plate is perpendicular to the second control part 1023, the second control part 1023 may be opened. On the contrary, the first control part 1013 may be opened when the first rotary plate rotates to be perpendicular to the first control part 1013. In this case, since the second rotary plate is parallel to the second control part 1023, the second control part 1023 may be closed.

The first transmission part 1011 or the second transmission part 1021 may be selectively opened or closed as the first and rotary plates rotate as described above.

Hereinafter, flow control valve units 11 and 12, which include control parts having different structures from the first or second control part 1013 or 1023 illustrated in FIG. 2, will be described with reference to FIGS. 3 and 4.

FIG. 3 is a schematic longitudinal sectional view of the flow control valve unit 11 according to Embodiment 2.

Referring to FIG. 3, the flow control valve unit 11 according to Embodiment 2 may include a first valve 111 and a second valve 112.

The first and second valves 111 and 112 may each be provided as the same check valve. In addition, the first and second valves may constitute the single flow control valve unit 11 by being coupled to be disposed in opposite directions.

Specifically, the first valve 111 may include a first transmission part 1111, a first opening/closing part 1112, and a first control part 1113.

The first transmission part 1111 may define a body of the first valve 111 and be a part through which air passes when the air is supplied into the lungs L from the air supply source O.

The first opening/closing part 1112 may be disposed in the first transmission part 1111 and rotate so that the air may flow only into the lungs L from the air supply source O. On the contrary, when the air flows in the direction in which the air is discharged from the lungs L, the first opening/closing part 1112 may be maintained in the closed state by being caught by a support part disposed in the first transmission part 1111.

The first control part 1113 may disposed in the first transmission part 1111, spaced apart from a hinge connection portion of the first opening/closing part 1112, and disposed adjacent to one side of the first opening/closing part 1112.

In addition, the first control part 1113 may include a locking element to fix the closed state of the first opening/closing part 1112 by rotating.

Specifically, the locking element has a "L" shape. One end of the locking element may be connected to a spring hinge, and the other end of the locking element may adjoin one side of the first opening/closing, part 1112 by freely rotating. The rotation of the locking element may be performed by a mechanical or electrical method from the outside of the first valve 111. Therefore, the first control part 1113 may control the flow of air through the first opening/closing part 1112. That is, when the locking element is rotated in a state in which the locking element does not adjoin the first opening/closing part 1112, the locking element is brought into contact with one side of the first opening/closing, part 1112 and fixed so that the first opening/closing part 1112 is not opened, thereby blocking the air supply path.

The second valve 112 may include a second transmission part 1121, a second opening/closing part 1122, and a second control part 1123.

The second transmission part 1121 may define a body of the second valve 112 and be a part through which air passes when the air is discharged from the inside of the lungs L.

The second opening/closing part 1122 may be disposed in the second transmission part 1121 and rotate so that the air may flow only to the outside O from the inside of the lungs L. On the contrary, when the air flows in the direction in which the air is supplied from the air supply source O, the opening/closing part 1122 may be maintained in the closed state by being caught by a support part disposed in the second transmission part 1121.

The second control part 1123 may be disposed in the second transmission part 1121, spaced apart from a hinge connection portion of the second opening/closing part 1122, and disposed adjacent to one side of the second opening/closing part 1122.

In addition, the second control part 1123 may include a locking element capable of locking the closed state of the second opening/closing part 1122.

Specifically, the locking element has an "L" shape. One end of the locking element may be connected to a spring hinge, and the other end of the locking element may adjoin one side of the second opening/closing part 1122 by freely rotating. The rotation of the locking element may be performed by a mechanical or electrical method from the outside of the second valve 112. Therefore, the second control part 1123 may control the flow of air through the second opening/closing part 1122. That is, when the locking element is rotated in a state in which the locking element does not adjoin the second opening/closing part 1122, the locking element is brought into contact with one side of the second opening/closing part 1122 and fixed so that the second opening/closing part 1122 is not opened, thereby blocking the air discharge path.

FIG. 4 is a schematic longitudinal sectional view of the flow control valve unit 12 according to Embodiment 3.

Referring to FIG. 4, the flow control valve unit 12 according to Embodiment 3 may include a first valve 121 and a second valve 122.

The first and second valves 121 and 122 may each be provided as the same check valve. In addition, the first and second valves 121 and 122 may be coupled to be disposed in opposite directions.

Specifically, the first valve 121 may include a first transmission part 1211, a first opening/closing part 1212, and a first control part 1213.

The first transmission part 1211 may define a body of the first valve 121 and be a part through which air passes when the air is supplied into the lungs L from the air supply source O.

The first opening/closing part 1212 may be disposed in the first transmission part 1211 and rotate so that the air flows only into the lungs L from the air supply source O.

The first control part 1213 may disposed in the first transmission part 1211, spaced apart from a hinge connection portion of the first opening/closing part 1212, and disposed adjacent to one side of the first opening/closing part 1212.

In addition, the first control part 1213 may include a locking element to fix the closed state of the first opening/closing part 1212 by sliding.

Specifically, the locking element may include a sliding member and a spring member.

A lower end of the sliding member is connected to the spring member so that the sliding member moves upward or downward, and a lateral surface of the sliding member may slide on one surface of the first opening/closing part 1212. The sliding member may be slid by a mechanical or electrical method from the outside of the first valve 121, Therefore, the first control part 1213 may control the flow of air through the first opening/closing part 1212. That is, the sliding member, which is positioned so as not to adjoin the first opening/closing part 1212, may be slid upward by being pushed by the spring member. The sliding member is brought into contact with one surface of the first opening/closing part 1212 and fixed so that the first opening/closing part 1212 is not opened, thereby blocking the air supply path.

The second valve 122 may include a second transmission part 1221, a second opening/closing part 1222, and a second control pail 1223.

The second transmission part 1221 may define a body of the second valve 122 and be a part through which air passes when the air is discharged from the inside of the lungs L.

The second opening/closing part 1222 may be disposed in the second transmission part 1221 and rotate so that the air may flow only to the outside O from the inside of the lungs L.

The second control part 1223 may be disposed in the second transmission part 1221, spaced apart from a hinge connection portion of the second opening/closing part 1222, and disposed adjacent to one side of the second opening/closing part 1222.

In addition, the second control part 1223 may include a locking element to lock the closed state of the second opening/closing part 1222 by sliding Specifically, the locking element may include a sliding member and a spring member.

A lower end of the sliding member is connected to the spring member so that the sliding member moves upward or downward, and a lateral surface of the sliding member may slide on one surface of the second opening/closing part 1222. The sliding member may be slid by a mechanical or electrical method from the outside of the second valve 122. Therefore, the second control part 1223 may control the flow of air through the second opening/closing part 1222. That is, the sliding member, which is positioned so as not to adjoin the second opening/closing part 1222, may be slid upward by being pushed by the spring member. The sliding member is brought into contact with one surface of the second opening/closing part 1222 and fixed so that the second opening/closing part 1222 is not opened, thereby blocking the air discharge path.

The artificial respirator 1 according to the embodiment may include a flow control valve unit 13 according to Embodiment 4 which is similar in configuration to the flow control valve unit 12 according to Embodiment 3 but different in structure from the first and second control parts 1213 and 1223.

FIG. 5 is a schematic transverse cross-sectional view of the flow control valve unit 13 according to Embodiment 4.

Referring to FIG. 5, the flow control valve unit 13 according to Embodiment 4 may include a first valve 131 and a second valve 122.

Although not illustrated in FIG. 5, the first and second valves 131 and 132 may each include a transmission part and an opening/closing part that are identical to the transmission parts 1211 and 1221 and the opening/closing parts 1212 and 1222 of the first and second valves 121 and 122 according to Embodiment 3.

In addition, the first valve 131 may include a first control part 1313, and the second valve 132 may include a second control part 1323.

As illustrated in FIG. 5, the flow control valve unit 13 may further include a rotary shaft 133 disposed between the first valve 131 and the second valve 132.

The rotary shaft 133 is a single shaft provided to be shared by the first and second control parts 1313 and 1323. The first and second control parts 1313 and 1323 may be connected by means of the rotary shaft 133 so as to move together.

Specifically, the first and second control parts 1313 and 1323 may be coupled at an angle at which any one of the first and second control parts 1313 and 1323 may be disposed to fix the closed state of the opening/closing part of the corresponding valve and the other of the first and second control parts 1313 and 1323 may be disposed to fix the opened state of the opening/closing part of the corresponding valve. Alternatively, an integrated control part having the above-mentioned shape may be provided.

The first and second control parts 1313 and 1323 may alternately open or close the air flow paths of the first and second valves 131 and 132 while rotating together about the rotary shaft 133.

Figure 5A:
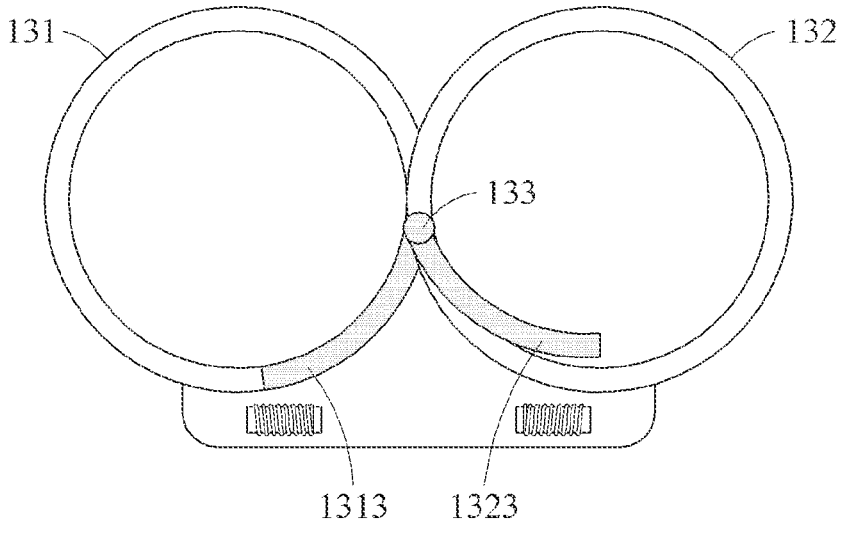
Figure 5B:
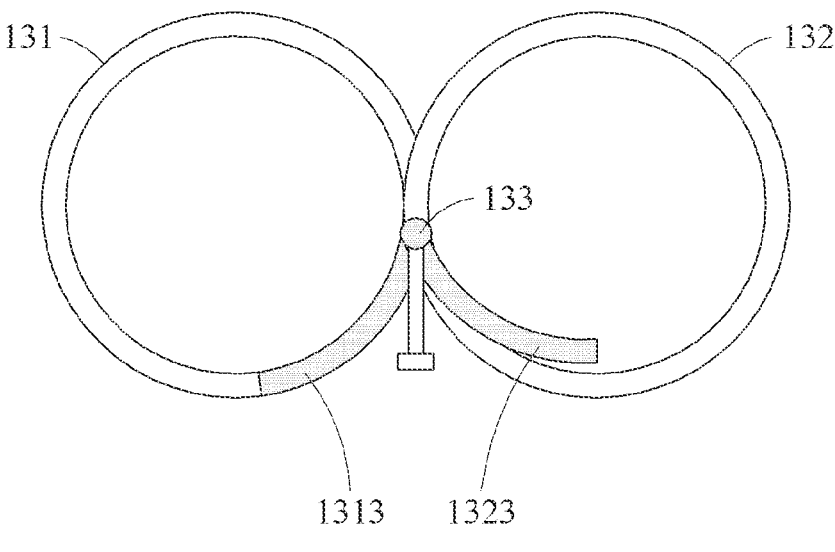

In addition, the operations of the first and second control parts 1313 and 1323 may be electromagnetically controlled by using an electromagnet, as illustrated in FIG. 5A, or mechanically controlled by using a gear, as illustrated in FIG. 5B.

As described above with reference to FIGS. 2 to 5, the artificial respirator 1 according to the embodiment may have the flow control units 10, 11, 12, and 13 and operate only in an exhalation direction during chest compression. In addition, after the predetermined time elapses or the chest compression is performed the predetermined number of times according to the preset air supply period, the air may naturally flow into the lungs by the negative pressure formed in the lungs. In this case, the flow control units 10, 11, 12, and 13 may operate only in the intake direction.

As the above-mentioned process is repeated, the artificial respirator 1 according to the embodiment may prevent an excessive amount of air from being introduced during the intake process. In addition, it is possible to prevent the damage to the lungs and the deterioration in chest compression effect due to the pressure the lungs during chest compression.

While the embodiments of the present invention have been described above with reference to particular contents such as specific constituent elements, the limited embodiments, and the drawings, but the embodiments are provided merely for the purpose of helping understand the present invention overall, and the present invention is not limited to the embodiment, and may be variously modified and altered from the disclosure by those skilled in the art to which the present invention pertains. For example, appropriate results may be achieved even though the described technologies are performed in different orders from the described method, the described constituent elements such as, the structures, the apparatuses, and the like are coupled or combined in different manners from the described method, and/or the constituent elements are substituted with or replaced by other constituent elements or equivalents. Accordingly, the spirit of the present invention should not be limited to the described embodiment, and all of the equivalents or equivalent modifications of the claims as well as the appended claims belong to the scope of the spirit of the present invention.

The invention claimed is:

1. A bidirectional flow-controllable artificial respirator comprising:
a chamber to store air;
a tube connected to the chamber such that the air flows therein;
a mask connected to the tube to be mounted around a face or oral cavity; and
a flow control valve unit disposed in the tube to control a flow of air between the mask and the chamber or an air supply source,
wherein the flow control valve unit comprises:
a first valve to allow an air supply path from the air supply source toward the mask, the first valve comprising:
a first transmission part through which the air passes when the air is supplied from the air supply source toward the mask;
a first opening/closing part disposed in the first transmission part to allow a flow only in one direction from the air supply source to the mask; and
a first control part disposed in the first transmission part and spaced apart from the first opening/closing part;
a second valve to allow an air discharge path from the mask to the outside of the artificial respirator, the second valve comprising:
a second transmission part through which the air passes when the air is discharged to the outside from the mask;
a second opening/closing part disposed in the second transmission part to allow a flow only in one direction from the mask to the outside; and

14 a second control part disposed in the second transmission part and spaced apart from the second opening/closing part, wherein the first and second valves are alternately opened or closed during artificial respiration, wherein the first valve is closed during chest compression so that negative pressure in a subject receiving air is maintained for a long period, and wherein the first and second valves are selectively opened or closed to allow a supply of air according to a preset air supply period; and
a measurement sensor disposed in the tube to measure a flow velocity of the air passing through the flow control valve unit or a pressure applied to a respiratory tract,
wherein when the supply of air is cut off during chest compression and when the pressure measured by the measurement sensor reaches a preset pressure during chest relaxation, the first control part selectively controls the supply of air through the first opening/closing part so that the supply of air is allowed according to the preset air supply period
wherein the second control part selectively controls a discharge of air through the second opening/closing part so that the discharge of air is allowed during chest compression and the discharge of air is cut off according to the preset air supply period,
wherein the first control part comprises a first rotary plate to open or close the first transmission part, the second control part comprises a second rotary plate to open or close the second transmission part, and the first and second rotary plates are disposed to be orthogonal to each other and rotate together by means of a rotary shaft to connect the first and second rotary plates.

2. The bidirectional flow-controllable artificial respirator of claim 1, wherein the first control part is closed during chest compression to cut off the supply of air through the first opening/closing part,
wherein the first control part is opened at a preset point in time of the supply of air to allow the supply of air through the first opening/closing part,
wherein the first control part is closed to maintain negative pressure in the subject receiving air for a long period when a point in time is not the point in time of the supply of air,
wherein the second control part is opened during chest compression to allow the discharge of air through the second opening/closing part,
wherein the second control part is closed at the preset point in time of the supply of air to cut off the discharge of air through the second opening/closing part, and
wherein the second control part is opened to improve efficiency in supplying air when a point in time is not the point in time of the supply of air.

3. The bidirectional flow-controllable artificial respirator of claim 1, wherein the first control part or the second control part comprises a single rotary plate to block an air transmission path.

4. The bidirectional flow-controllable artificial respirator of claim 1, wherein the first control part or the second control part comprises a locking element to fix a closed state of the first opening/closing part or the second opening/closing part.

5. The bidirectional flow-controllable artificial respirator of claim 4, wherein the locking element fixes the closed state of the first opening/closing part or the second opening/closing part by rotating.

6. The bidirectional flow-controllable artificial respirator of claim 4, wherein the locking element fixes the closed state of the first opening/closing part or the second opening/closing part by sliding.

* * * * *